United States Patent [19]

Suzuki et al.

[11] Patent Number: 5,237,077

[45] Date of Patent: Aug. 17, 1993

[54] NON-POLLUTIONAL PROCESS FOR PRODUCING AROMATIC NITRO COMPOUNDS WITHOUT USING A MINERAL ACID

[75] Inventors: Hitomi Suzuki, Matsuyama; Takashi Murashima, Yamatotakada; Kenkichi Tsukamoto, Higashikurume, all of Japan

[73] Assignee: Nippon Kayaku Kabushiki Kaisha, Tokyo, Japan

[21] Appl. No.: 844,587

[22] PCT Filed: Aug. 29, 1991

[86] PCT No.: PCT/JP91/01151
§ 371 Date: Mar. 27, 1992
§ 102(e) Date: Mar. 27, 1992

[87] PCT Pub. No.: WO92/04313
PCT Pub. Date: Mar. 19, 1992

[30] Foreign Application Priority Data

Aug. 29, 1990 [JP] Japan .................................. 2-225110
Feb. 21, 1991 [JP] Japan .................................. 3-047322

[51] Int. Cl.$^5$ ....................... C07C 97/18; C07C 97/24
[52] U.S. Cl. ................................. 552/210; 552/236; 552/238; 564/218; 568/927; 568/929; 568/930; 568/931; 568/933; 568/934; 568/935; 568/937; 568/938; 568/939; 568/940
[58] Field of Search ............... 568/929, 930, 933, 934, 568/935, 937, 938, 939, 940, 927, 931; 552/210, 236, 238; 564/218

[56] References Cited

PUBLICATIONS

Suzuki, et al., *Chemistry Letters*, No. 5 (1991) pp. 817–818.

*Primary Examiner*—Marianne M. Cintins
*Assistant Examiner*—Kimberly J. Kestler
*Attorney, Agent, or Firm*—Nields & Lemack

[57] ABSTRACT

The present invention relates to a process for producing an aromatic nitro compound by introducing a nitrogen oxide gas and ozone-containing oxygen or air into a halogenated organic solvent dissolving or suspending therein an aromatic compound, thereby subjecting the aromatic compound to nitration. By the use of a system comprising the nitrogen oxide and ozone-containing oxygen or air as the nitrating agent, the aromatic nitro compound can be produced under mild conditions without using any mineral acid. In addition, the various disadvantages due to the use of mineral acid in the conventional process can be avoided by the process of the present invention.

4 Claims, 1 Drawing Sheet

NON-POLLUTIONAL PROCESS FOR PRODUCING AROMATIC NITRO COMPOUNDS WITHOUT USING A MINERAL ACID

DESCRIPTION

1. Technical Field

The present invention relates to a process for producing aromatic nitro compounds. More particularly, the invention relates to a process for producing aromatic nitro compounds without using nitric acid or a nitric acid derivative as a direct nitrating agent.

2. Background Art

An aromatic nitro compound is an essential substance as the starting material for the production of a wide variety of typical organic industrial products such as pharmaceuticals, agricultural chemicals, plastics and explosives. For the industrial synthesis of these compounds, ever since the last century, there has been employed a method in which nitric acid is used either singly or in combination with other acid catalyst (sulfuric acid, phosphoric acid, etc.) as nitrating agent.

In this method, however, since a large amount of a highly concentrated acid is used, there are always involved the technical problems to be solved, which vary in nature according to the aromatic substrate to be nitrated, due to the disadvantage in nitration using nitric acid. Such problems include an exothermic reaction under the heterogeneous conditions in addition to danger in operation, treatment of a large amount of waste acid, use of a corrosion-resistant apparatus, difficulties in achieving continuous automation, tremendous heat generation and oxidation of the substrate.

Generally, the nitration reactions of aromatic compounds proceed with the nitronium ions ($NO_2^+$) as the reaction species which is generated in the course of the reaction shown by the following formula, so the single use of nitric acid can not provide a satisfactory nitration and it is therefore necessary to combinedly use a strong acid as auxiliary agent for converting nitric acid into acidinium ion ($H_2NO_3^+$):

$$HNO_3 + H^+ \rightarrow (H_2NO_3^+) \rightarrow H_2O + NO_2^+$$

Concentrated sulfuric acid or fuming sulfuric acid is industrially used for this purpose, but great cost is required for recovery or treatment of the acid after completion of nitration, and also a large amount of water or an alkaline agent is necessitated for neutralization and washing of the product. Furthermore, since the reaction is carried out under a strongly acidic condition, side reactions involving the carbocation species or radical cation species generated competitively in the course of the reaction are unavoidable. Intermixing of the various water- or oil-soluble organic compounds produced through the side reactions into waste water is a serious problem that could not be overlooked from the standpoint of environmental pollution.

It has been desired to establish a process for effectively producing aromatic nitro compounds without using any inorganic acid, which is troublesome to handle, such as nitric acid, sulfuric acid, phosphoric acid, etc., and with minimized environmental pollution.

DISCLOSURE OF INVENTION

The present inventors have found that the nitrogen oxides, most typically nitrogen dioxide, exhibit a strong nitrating function in the presence of ozone. That is, the present inventors have found that an aromatic compound can be directly nitrated by introducing a gaseous nitrogen oxide and ozone-containing (ozonized) oxygen or air into a chemically stable organic solvent having been dissolved or suspended therein the aromatic compound and making the nitrogen oxide act to the aromatic compound, under a mild condition at a temperature around room temperature. The present invention was attained on the basis of this finding.

Thus, the present invention provides:

(1) a process for producing an aromatic nitro compound which comprises dissolving or suspending an aromatic compound in a halogenated organic solvent, and introducing into the resulting solution or suspension a nitrogen oxide and ozone-containing oxygen or air, thereby nitrating the aromatic compound; and (2) a process set forth in (1) wherein the nitration is carried out in the presence of a solid phase carrier, a cation exchange resin or a Lewis acid.

The present invention will be described in detail below.

According to the process of the present invention, it is possible to effectuate not only mononitration but also polynitration such as dinitration and trinitration as desired by properly selecting the reaction conditions. The position substituted by the nitro group (orientation) is, as in the case of using nitric acid as nitrating agent, dependent on the rule in electrophilic reactions. That is, an aromatic compound having an electron donative group represented by alkyl group shows ortho- or para-orientation and an aromatic compound having an electron attractive group represented by nitro group shows meta-orientation, but in both cases the extent of the orientation is slightly weaker than in case of using nitric acid as nitrating agent.

Examples of the aromatic compounds which can be used as the starting material in the process of the present invention include benzene, toluene, (o-, m- or p-)xylene and their mononitro and dinitro compounds; benzenes substituted by one or more of alkyl groups having one or more of carbon atoms, and their mononitro and dinitro compounds; halogenated benzenes such as monochlorobenzene, dichlorobenzene, trichlorobenzene, etc., and their mononitro and dinitro compounds; benzenes substituted by alkyl group and halogen, and their mononitro and dinitro compounds; benzenes substituted by alkoxy group and their mononitro and dinitro compounds; naphthalene and its derivatives; anthracene and its derivatives; anthraquinone and its derivatives; pyrene and its derivatives; and acetanilide derivatives which is optionally substituted with alkyl group, alkoxy group or halogen.

The halogenated organic solvent used as solvent in the process of the present invention needs to be stable to the nitrogen oxide used as the reacting agent. A halogenated aliphatic compounds are preferably used, and dichloromethane and tetrachloromethane can be mentioned as preferred examples of such halogenated aliphatic compounds. Two or more of the solvents may be used in admixture. The amount of the solvent used is usually 2 to 200 times, preferably 5 to 100 times (by weight) the amount of the aromatic compound used as starting material (reaction substrate). Nitrogen tetraoxide, nitrogen dioxide or the like is used as the nitrogen oxide. Such nitrogen oxides may be used in admixture. The gas of such nitrogen oxide can be produced, for example, by oxidizing a mixed gas of air and ammonia at a temperature of, for example, 500° to 700° C. in the presence of a catalyst (such as platinum, platinum/rhodium or the like).

Ozone-containing oxygen or air can be obtained by, for example, passing oxygen or air through a silent discharge tube.

The aromatic nitro compounds are produced, for instance, in the following way.

First, the starting aromatic compound is dissolved or suspended in the halogenated organic solvent as mentioned above at a temperature below room temperature (e.g. 10° to 30° C.), preferably under cooling with ice (at 0° to −30° C. for instance). Then a gaseous nitrogen oxide and ozone-containing oxygen or air obtained by passing oxygen or air through a silent discharge tube are blown into the thus formed solution or suspension under stirring. Ozone-containing oxygen or air is preferably blown into said solution or suspension in the form of fine bubbles by using, for example, sintered glass balls. The amounts of the nitrogen oxide and ozone-containing oxygen or air to be introduced is not specifically restricted. Such amounts are properly adjusted according to the produced amount of the desired aromatic nitro compound by analyzing the reaction solution by gas chromatography. For instance, in the case of mononitration, the amounts to be introduced are so selected that they will be one molar equivalent or more to the aromatic compound, and in the case of dinitration, the amounts are selected so that they will be 2 molar equivalents or more to the aromatic compound. In case formation of many isomers is expected, the introduction of the gas may be discontinued when one equivalent or less of the gas is introduced to terminate the reaction with a part of the starting aromatic compound being left unreacted. The flow of the nitrogen oxide and ozone-containing oxygen or air are also adjusted to be in an appropriate range based on the produced amount of the desired aromatic nitro compound by analyzing the reaction solution by gas chromatography.

The reaction temperature is usually room temperature or below, but in case the starting material used is of low reactivity, the reaction is preferably carried out under moderate heating (for example at 40° to 50° C.). The reaction time is decided by analyzing the amount of the objective substance (the aromatic nitro compound) in the reaction mixture by, for instance, gas chromatography. For obtaining a polynitro compound according to the conventional methods, heating is generally required, but according to the process of the present invention, it is possible to accomplish polynitration by elongation of the reaction time (gas blowing time). Polynitration according to the process of the present invention is preferably applied to the aromatic compounds having aromatic rings with high reactivity.

The reaction may be accomplished either according to an ordinary batch process or according to a continuous process in which the nitrogen oxide and ozone-containing oxygen or air are blown into a first reactor of a plural of reactors and the excess gas released from the first reactor is led into a second reactor, and so forth. In this way, the nitrogen oxide is perfectly consumed.

Further, in the process of the present invention, a solid phase carrier such as molecular sieves, a cation exchange resin such as fluorine ion exchange resin, and a Lewis acid such as boron trifluoride etherate, silver oxide, methanesulfonic acid or the like may be added into the reaction system as a catalyst. The catalyst is usually added in an amount of 0.1 to 20 mol % based on the starting aromatic compound (reaction substrate). Additive property can be expected in the combined use of the catalysts.

After the reaction is completed, the solvent is removed from the reaction mixture by distillation, filtration or other means, if necessary after neutralizing the reaction mixture, and the residue is subjected to an ordinary treatment such as fractional distillation, recrystallization, etc. to obtain the objective substance (the aromatic nitro compound) in a good yield. Purity of the objective substance can be determined by gas chromatography. The used solvent may be recycled after removing the by-product nitric acid and the remaining nitrogen oxide.

The process of the present invention has the advantages that consumption of heat is small because of low reaction temperature, and that the reaction conditions are easily set according to the type of the starting material to be nitrated and the type of the reaction to be performed (mononitration or polynitration) since the ozone concentration can be easily adjusted by changing the silent discharge voltage of the ozone generator. The process of the present invention also has the advantage that the solvent used in the reaction can be reused after removing the by-product nitric acid or the remaining nitrogen oxide by washing with a sodium carbonate aqueous solution containing urea or by passing through a sodium carbonate powder layer.

BEST MODE FOR CARRYING OUT THE INVENTION

Figure 1:
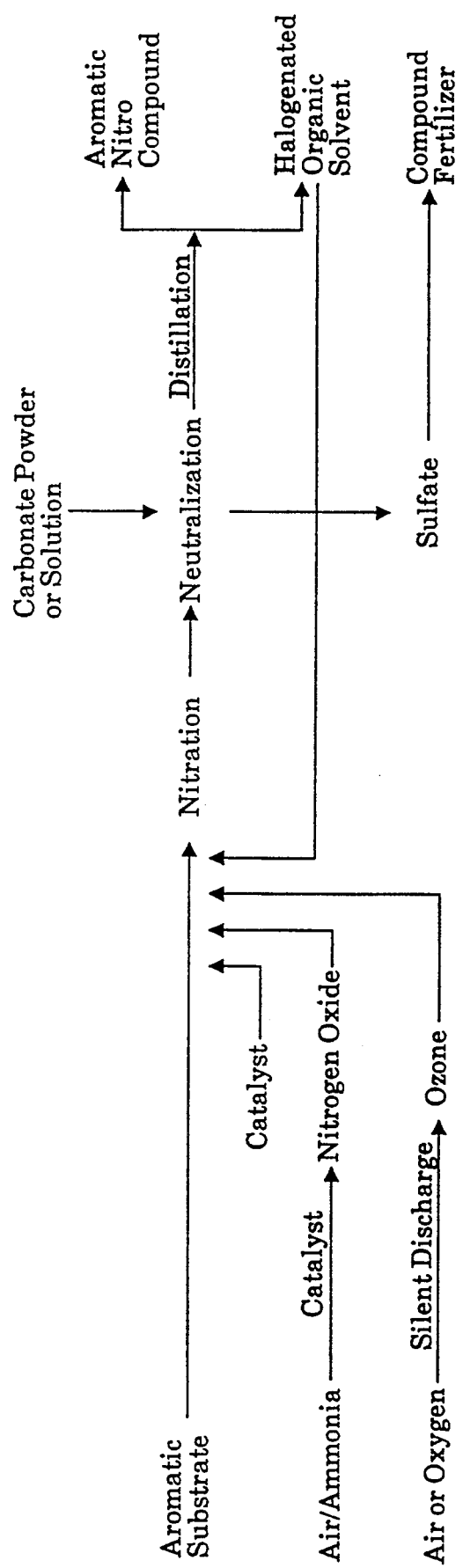
FIG. 1 is a diagram illustrating an example of the process for obtaining the aromatic nitro compound from the aromatic compound through nitration by the actions of the nitrogen oxide, ozone and a catalyst, and recycling of the solvent and utilization of the by-product.

The process of the present invention will be illustrated more particularly with reference to the examples thereof.

EXAMPLES 1-3

In 30 ml of dried dichloromethane was dissolved 5 ml of toluene, and the solution was put into a pyrex three-necked flask and cooled to −10° C. Then nitrogen dioxide gas was introduced into the solution from an inlet while introducing ozone-containing oxygen from another inlet, thereby carrying out the reaction for 3 hours. After the reaction, the nitrogen oxide existing dissolved in the reaction mixture was removed by passing air through the reaction mixture, then the reaction mixture was washed with a sodium carbonate aqueous solution and the solvent was removed to obtain nitrotoluenes. The yield of the obtained mononitrotoluene and the composition of the isomers were as shown below. In Examples 2 and 3, the reaction was conducted by adding into the reaction system molecular sieves 4A or boron trifluoride etherate, respectively, followed by the same post-treatments as described above.

|  | Composition of Isomers (%) | | | |
|---|---|---|---|---|
| Catalyst | Ortho | Meta | Para | Yield (%) |
| Ex. 1 None | 57.0 | 2.4 | 40.0 | 57 |
| Ex. 2 Molecular sieves 4A | 57.3 | 3.0 | 39.7 | 76 |

-continued

| | Catalyst | Composition of Isomers (%) | | | Yield (%) |
|---|---|---|---|---|---|
| | | Ortho | Meta | Para | |
| Ex. 3 | Boron trifluoride etherate | 57.4 | 3.1 | 39.5 | 78 |

EXAMPLE 4

In 50 ml of dichloromethane was dissolved 5 g of p-nitrotoluene and the solution was cooled to 31 10° C. (using a pyrex three-necked flask). Thereafter, there were performed the same operations as in Example 1 to obtain 2,4-dinitrotoluene in a yield above 90%.

EXAMPLE 5

In 50 ml of dichloromethane was dissolved 5 g of benzene and the solution was put into a pyrex three-necked flask and cooled to −10° C. Then nitrogen dioxide gas was introduced into the solution from an inlet while ozone-containing oxygen was introduced from another inlet to carry out the reaction for 3 hours. After the reaction, the nitrogen oxide existing dissolved in the reaction mixture was removed by passing air through the reaction mixture, then the reaction mixture was washed with a sodium carbonate aqueous solution and the solvent was removed to obtain a mixture of benzene, nitrobenzene and dinitrobenzene. The yield of the obtained crude product and the composition of the isomers are as shown below.

| Yield | 81.0% |
|---|---|
| Composition (%) | |
| Unreacted compound | 50.0 |
| Nitrobenzene | 46.5 |
| m-dinitrobenzene | 2.3 |
| p-dinitrobenzene | 1.1 |
| o-dinitrobenzene | ≦0.1 |

EXAMPLE 6

Into a pyrex three-necked flask were placed 30 ml of dichloromethane, 5 ml of toluene and 75 mg of silver oxide and the mixture was subjected to the same treatments as in Example 1 to obtain 7.2 g of a crude product. The composition of the crude product determined by gas chromatography is shown below.

| Yield | 99.6% |
|---|---|
| Composition (%) | |
| Unreacted compound | 0.4 |
| o-nitrotoluene | 55.2 |
| m-nitrotoluene | 3.3 |
| p-nitrotoluene | 41.5 |
| Dinitrotoluene | — |

EXAMPLE 7

In 50 ml of dichloromethane was dissolved 5 g of chlorobenzene and the solution was put into a pyrex three-necked flask and cooled to −10° C. Then nitrogen dioxide was introduced into the solution from an inlet while ozone-containing oxygen was introduced from another inlet to carry out the reaction for 3 hours. The resulting reaction mixture was subjected to the same treatments as in Example 1 to obtain chloronitrobenzenes.

| Yield | 61.2% |
|---|---|
| Composition (%) | |
| o-chloronitrobenzene | 46.1 |
| m-chloronitrobenzene | 1.1 |
| p-chloronitrobenzene | 52.8 |

EXAMPLE 8

To 50 ml of dried dichloromethane was added 5 g of benzoic acid and the mixture was cooled to −10° C. (using a pyrex three-necked flask). Nitrogen dioxide gas was introduced into the mixture from an inlet while ozone-containing oxygen was introduced from another inlet to carry out the reaction for 3 hours. After the reaction, the nitrogen oxide existing dissolved in the reaction mixture was removed by passing air through the reaction mixture and the solvent was distilled away. To the residue was added 20 ml of methanol and the solution was refluxed for 4 hours to convert the product to methyl esters. Then the solvent was removed to obtain 7 g of the crude product. Yield was 95%.

Gas chromatographic analysis of the product showed the following composition.

| Composition (%) | |
|---|---|
| Methyl benzoate | 7.8 |
| Methyl o-nitrobenzoate | 6.1 |
| Methyl p-nitrobenzoate | 1.8 |
| Methyl m-nitrobenzoate | 84.3 |

EXAMPLE 9

In 50 ml of dry dichloromethane was suspended 0.5 g of anthraquinone and the suspension was cooled to −10° C. (using a pyrex three-necked flask). To the suspension was added to 50 mg (20 mol %) of methanesulfonic acid, and then nitrogen dioxide gas was introduced into the suspension from an inlet while ozone-containing oxygen was introduced from another inlet for a period of 3 hours to carry out the reaction. Thereafter, the nitrogen oxide existing dissolved in the reaction mixture was removed by passing air through the reaction mixture and then the solvent was removed to obtain 0.58 g of a crude nitro compounds (yield: 95%).

Gas chromatographic analysis of the product showed the following composition.

| Composition (%) | |
|---|---|
| Anthraquinone (unreacted compound) | 14.9 |
| β-nitroanthraquinone | 8.8 |
| α-nitroanthraquinone | 76.2 |

This crude product was purified by column chromatography to obtain pure α-nitroanthraquinone.

EXAMPLE 10

In a pyrex three-necked flask was paced 50 ml of dry dichloromethane. Then 0.5 g of α-nitronaphthalene was added thereinto and the mixture was cooled to −10° C. Nitrogen dioxide was blown into the mixture from an inlet while ozone-containing oxygen was blown from another inlet for a period of 3 hours. After completion of the reaction, air was blown into the reaction mixture to drive out the excess nitrogen dioxide. Then the solvent was distilled away to obtain 0.6 g of crude dinitronaphthalenes (yield: 95%).

Gas chromatrographic analysis of the product showed the following composition.

| Composition (%) | |
| --- | --- |
| 1,5-dinitronaphthalene | 21.7 |
| 1,8-dinitronaphthalene | 58.8 |
| Dinitronaphthalene other than 1,8- and 1,5-isomer | 1.7 |
| Trinitronaphthalene | 18.3 |

EXAMPLE 11

To 50 ml of chloroform was added 1.35 g of acetanilide, and the mixture was placed into a pyrex three-necked flask and cooled to −10° C. Nitrogen dioxide was introduced into the mixture from an inlet while introducing ozone-containing oxygen from another inlet to carry out the reaction for 2.5 hours. The reaction mixture was subjected to the same treatments as in Example 1 to obtain 1.6 g of nitroacetanilides. Gas chromatographic analysis of the product showed the following composition.

| Composition (%) | |
| --- | --- |
| o-nitroacetanilide | 80.1 |
| p-nitroacetanilide | 12.9 |
| Dinitroacetanilides | 7.0 |

EXAMPLE 12

To 50 ml of chloroform was added 1.35 g of acetanilide, and the mixture was placed into a pyrex three-necked flask and cooled to −10° C. Nitrogen dioxide was introduced into the mixture from an inlet while introducing ozone-containing oxygen from another inlet to carry out the reaction for 3 hours. The reaction mixture was subjected to the same treatments as in Example 1 to obtain 2.2 g of nitroacetanilides. Gas chromatographic analysis of the product showed the following composition.

| Composition (%) | |
| --- | --- |
| Mononitroacetanilides | 0.6 |
| 2,4-dinitroacetanilide | 81.0 |
| 2,6-dinitroacetanilide | 18.4 |

EXAMPLE 13

In 50 ml of dichloromethane was dissolved 5.0 g of each of t-butylbenzene, isopropylbenzene and ethylbenzene and each solution was put into a three-necked flask and cooled to −10° C. Nitrogen dioxide was introduced into the solution from an inlet while ozone-containing oxygen was introduced from another inlet to carry out the reaction for 3 hours. The reaction mixture was subjected to the same treatments as in Example 1 to obtain the nitro compounds in the respective yields shown below. Gas chromatographic (GC) analyses of the products showed the following compositions.

| Starting material | Yield of product (g) |
| --- | --- |
| (a) t-butylbenzene | 6.6 |
| (b) Isopropylbenzene | 6.5 |
| (c) Ethylbenzene | 5.6 |

| | Composition (%) | | | |
| --- | --- | --- | --- | --- |
| | Results of GC analyses | | | |
| Starting material | o-nitro isomer | m-nitro isomer | p-nitro isomer | Others |
| (a) | 12.3 | 5.8 | 79.3 | 2.6 |
| (b) | 22.2 | 3.4 | 68.6 | 5.8 |
| (c) | 41.9 | 2.4 | 50.4 | 5.3 |

EXAMPLE 14

To 50 ml of dry dichloromethane was added 5.0 g of 5-t-butyl-3-xylene and 500 mg of methanesulfonic acid and the mixture was put into a three-necked flask and cooled to 10° C. Nitrogen dioxide gas was introduced into the mixture from an inlet while ozone-containing oxygen was introduced from another inlet to carry our the reaction for 3 hours. The reaction mixture was subjected to the same treatments as in Example 1 to obtain 6.5 g of a product. Gas chromatographic analysis of the product showed the following composition.

| Composition (%) | |
| --- | --- |
| 2-nitro-5-t-butyl-3-xylene | 55.1 |
| 4-nitro-5-t-butyl-3-xylene | 12.9 |
| 2,4-dinitro-5-t-butyl-3-xylene | 15.6 |
| 4,6-dinitro-5-t-butyl-3-xylene | 5.5 |
| Others | 10.9 |

EXAMPLE 15

To 50 ml of dry dichloromethane was added 5.0 g of 5-t-butyl-3-xylene and 500 mg of methanesulfonic acid, and the mixture was put into a three-necked flask and cooled to −10° C. Nitrogen dioxide gas was introduced into the mixture from an inlet while ozone-containing oxygen was introduced from another inlet to carry out the reaction for 12 hours. Air was blown into the reaction mixture to drive out the excess nitrogen dioxide and 7.3 g of crystals was isolated. This product was found to be 2,4,6- trinitro-5- t-butyl-3-xylene.

EXAMPLE 16

To 50 ml of dry dichloromethane were added 0.5 g of anthraquinone and 50 mg of methyl disulfide, and the mixture was put into a three-necked flask and cooled to 31 10° C. Nitrogen dioxide gas was introduced into the mixture from an inlet while ozone-containing oxygen was introduced from another inlet to carry out the reaction for 12 hours. Then the nitrogen dioxide was removed in the same manner as in Example 9 and the solvent was distilled away to obtain 0.55 g of crude nitro compounds.

Gas chromatographic analysis of the product showed the following composition.

| Composition (%) | |
| --- | --- |
| Anthraquinone (unreacted compound) | trace |
| 2-nitroanthraquinone | 5.4 |
| 1-nitroanthraquinone | 7.7 |
| 1,8-dinitroanthraquinone | 52.5 |
| 1,5-dinitroanthraquinone | 11.3 |
| 1,6- or 1,7-dinitroanthraquinone | 20.6 |

| Composition (%) | |
| --- | --- |
| 2,6- or 2,7-dinitroanthraquinone | 0.8 |

INDUSTRIAL APPLICABILITY

According to the process of the present invention, the aromatic nitro compounds, which are important as starting material for producing the organic industrial products, can be produced under the mild conditions without using any mineral acid. Also, the process of this invention has little risk of causing pollution and is therefore favorable from the viewpoint of environmental protection.

We claim:

1. A process for producing an aromatic nitro compound which comprises dissolving or suspending an aromatic compound in a halogenated organic solvent, and introducing into the resulting solution or suspension a nitrogen oxide gas and ozone-containing oxygen or air, thereby subjecting the aromatic compound to nitration.

2. The process according to claim 1, wherein the nitration is carried out in the presence of a solid phase carrier, a cation exchange resin or a Lewis acid.

3. The process of claim 2, wherein said aromatic compound is selected from the group consisting of benzene and its mononitro and dinitro compounds, toluene and its mononitro and dinitro compounds, o-xylene and its mononitro and dinitro compounds, m-xylene and its mononitro and dinitro compounds, p-xylene and its mononitro and dinitro compounds, benzene substituted by one or more alkyl groups having one or more carbon atoms, and its mononitro and dinitro compounds, halogenated benzene and its mononitro and dinitro compounds, benzene substituted by an alkyl group and halogen, and its mononitro and dinitro compounds, benzene substituted by an alkoxy group and its mononitro and dinitro compounds, naphthalene, anthracene, anthraquinone, pyrene and acetanilide optionally substituted with alkyl, alkoxy or halogen.

4. The process of claim 1, wherein said aromatic compound is selected from the group consisting of benzene and its mononitro and dinitro compounds, toluene and its mononitro and dinitro compounds, o-xylene and its mononitro and dinitro compounds, m-xylene and its mononitro and dinitro compounds, p-xylene and its mononitro and dinitro compounds, benzene substituted by one or more alkyl groups having one or more carbon atoms, and its mononitro and dinitro compounds, halogenated benzene and its mononitro and dinitro compounds, benzene substituted by an alkyl group and halogen, and its mononitro and dinitro compounds, benzene substituted by an alkoxy group and its mononitro and dinitro compounds, naphthalene, anthracene, anthraquionone, pyrene and acetanilide optionally substituted with alkyl, alkoxy or halogen.

* * * * *